US005728690A

United States Patent [19]

Chen

[11] Patent Number: 5,728,690
[45] Date of Patent: Mar. 17, 1998

[54] CLEAR NON-ALCOHOLIC HYDROCORTISONE SOLUTIONS

[75] Inventor: Gloria Yoshiko Chen, Hammonton, N.J.

[73] Assignee: American Home Products Corporation, Madison, N.J.

[21] Appl. No.: 617,465

[22] Filed: Mar. 18, 1996

Related U.S. Application Data

[63] Continuation of Ser. No. 367,387, Dec. 30, 1994, abandoned.

[51] Int. Cl.$^6$ .................... A61K 31/56; A61K 31/74
[52] U.S. Cl. .................... 514/179; 424/78.05; 514/975; 514/424; 514/400; 514/952; 514/970; 514/973
[58] Field of Search .................... 514/179, 424, 514/400, 952, 970, 973, 975; 424/78.05

[56] References Cited

U.S. PATENT DOCUMENTS

| | | | |
|---|---|---|---|
| 2,280,130 | 3/1942 | Johnson | 167/65 |
| 4,213,979 | 7/1980 | Levin | 424/243 |
| 4,289,764 | 9/1981 | Yarrow | 424/243 |
| 4,305,936 | 12/1981 | Klein | 424/242 |
| 4,383,992 | 5/1983 | Lipari | 424/238 |
| 4,788,060 | 11/1988 | Endicott et al. | 424/443 |
| 4,813,023 | 3/1989 | Garlen | 514/169 |
| 5,190,936 | 3/1993 | Laugier et al. | 514/169 |
| 5,229,370 | 7/1993 | Ammeral | 514/26 |

OTHER PUBLICATIONS

V. Das Gupta, Drug Development and Industrial Pharmacy 11(12), 2083097 (1985).
Hajratwala, J. Pharm. Pharmacology 28, 934 (1976).
Barry, J. Pharm. Pharmacology 28, 210 (1976).

*Primary Examiner*—Theordore J. Criares
*Attorney, Agent, or Firm*—R.F. Boswell, Jr.

[57] ABSTRACT

This invention relates to clear aqueous solutions of hydrocortisone which are free of lower alcohols. When applied to the skin, either directly or by wipe, the solution is practically invisible and has a further advantage that the solution will not irritate or dry the skin or give the stinging sensation of an alcohol containing solution. Dissolution of hydrocortisone without alcohol is accomplished by using the anionic surfactant sodium dioctyl sulfosuccinate in mixtures of glycerin, propylene glycol and polyethylene glycol diluted to final volume with water.

11 Claims, No Drawings

CLEAR NON-ALCOHOLIC HYDROCORTISONE SOLUTIONS

This is a continuation, of application Ser. No. 08/367,387, filed Dec. 30, 1994, now abandoned.

FIELD OF THE INVENTION

This invention relates to clear alcohol-free hydrocortisone compositions which are useful for external treatment of skin irritations, itching, and rashes. The solubilization of hydrocortisone in a mixture of non-volatile organic co-solvents is accomplished by adding the anionic surfactant sodium dioctyl sulfosuccinate (docusate sodium). The product can be applied to the skin as a liquid or gel or with towelettes or wipes pre-moistened with an invention hydrocortisone solution. Hydrocortisone is approved in up to a one percent concentration for non-prescription pharmaceutical products.

BACKGROUND OF THE INVENTION

Hydrocortisone is used in many topical preparations as a treatment for temporary relief of itching associated with minor skin irritation, inflammation and rashes due to eczema, insect bites, poison ivy, poison oak, poison sumac, soaps, detergents, cosmetics, seborrheic dermatitis, psoriasis and itching in the genital and anal areas of the body. Hydrocortisone has very little solubility in water, only 28 mg of hydrocortisone per 100 ml of water (Merck Index, Eleventh Edition). Because of the limited solubility of hydrocortisone in water (0.028% on a weight/volume basis), it is necessary to add co-solvents, surfactants, and/or complexing agents to obtain an aqueous solution of hydrocortisone in sufficient concentration so as to be useful in treating the conditions for which topical hydrocortisone is indicated. Hydrocortisone is often formulated as a suspension or emulsion in the form of a lotion or cream base which may not be permanently homogeneous.

Because of the low solubility of hydrocortisone, preparation of clear solutions of hydrocortisone at 1–2% concentrations is difficult. Co-solvents such as a lower molecular weight alcohol (ethyl alcohol, isopropyl alcohol) may be added to increase solubility or surfactants may be added to form emulsions of the oil-in-water or water-in-oil type. U.S. Pat. No. 2,880,130 discloses the use of polyoxyethylene sorbitan monooleate (Tween 80®) in amounts of from 2–25 percent of the vehicle to obtain clear aqueous solutions containing up to 0.2% of hydrocortisone. U.S. Pat. No. 4,289,764 describes formulations containing 0.025 to 0.4% hydrocortisone in an aqueous 15–50% propylene glycol solution acidified to pH 2.7–3.3 with a non-toxic organic acid such as citric acid. U.S. Pat. No. 4,305,936 provides for a 0.005–2.5% hydrocortisone clear liquid formulation containing 1–4% by weight of a glyceryl ester of fatty acids having 6–22 carbon atoms, 1–3% by weight of the hydrocortisone of a betaine surfactant, and 10–50% of an alkanol co-solvent, preferably ethanol. U.S. Pat. No. 4,778,060 describes a 0.5% hydrocortisone aqueous solution for use as a douche and for impregnating toiletries for wipes. The solution also contains caprylic/capric triglycerides (5–20%), sorbitan stearate (2–4%), Polysorbate 60® (1–3%), preservatives and citric acid.

U.S. Pat. No. 4,383,992 discloses an aqueous solution of an inclusion complex of unbranched beta-cyclodextrin and hydrocortisone and reveals that the inclusion complex must dissociate before the hydrocortisone is physiologically active. U.S. Pat. No. 5,229,370 discloses an aqueous solution on an inclusion complex composed of a branched beta-cyclodextrin and hydrocortisone. The branched beta-cyclodextrin inclusion complex appears to incorporate greater amounts of hydrocortisone than the unbranched beta-cyclodextrin of the previous patent.

The unexamined Japanese patent application JP 05170643 discloses micellar ophthalmic preparations containing 0.5–1.0% water insoluble steroid, a non-ionic surfactant, polyalcohols and water.

V. Das Gupta, *Drug Development and Industrial Pharmacy* 11(12), 2083–2097 (1985) reported that the anionic surfactant sodium lauryl sulfate adversely affected the stability of hydrocortisone solutions in aqueous ethanolic solutions of hydrocortisone also containing glycerin and/or propylene glycol.

SUMMARY OF THE INVENTION

The invention provides hydrocortisone solutions free of lower alcohols such as ethanol, propanol or isopropanol for topical use and a process for preparation of the alcohol-free solutions. An alcohol free preparation is less likely to irritate or dry the skin or burn when applied at the affected area of the skin. The invention also provides for hydrocortisone solutions which are colorless and thus are less visible on the skin than non-colorless preparations. The invention further provides for hydrocortisone solutions which are stable and homogenous and which have a pH that is compatible with the skin in a human.

The invention solutions of hydrocortisone can be applied externally to the skin as a liquid by rubbing the liquid composition on the skin or applying the hydrocortisone solution with an applicator such as a spongy material, a roll-on applicator, a spray or a hydrocortisone solution-impregnated absorbent wipe. Wipes are conveniently prepared by impregnating a soft tissue such as a rayon web bonded with an acrylic copolymer binder or a 60% wool pulp, 30% rayon, 10% polyester/polyethylene blend with a clear alcohol-free solution of hydrocortisone according to the present invention. Formulation of the invention solution into a gel or more viscous solution for convenience in application is contemplated. The viscosity of the solution can be increased by adding to the solution one or more thickening adjuvants known in the art such as an acrylic acid polymer, hydroxyethylcellulose, hydroxypropylcellulose and the like. Incorporation of a fragrance in the invention composition is also contemplated. Further contemplated is addition of effective amounts of approved topical dermatological agents. These agents comprise an antibiotic such as polymixin B sulfate, bacitracin zinc or neomycin sulfate to prevent or alleviate infection, an antihistamine such as benadryl to alleviate itching, a topical anesthetic such as zylocaine or benzocaine to alleviate pain or a sunscreen to protect the treated area of the skin from ultraviolet light damage. Such additives would aid in reducing discomfort due to swelling and itching and pain and help in treating or preventing skin infection.

DETAILED DESCRIPTION OF THE INVENTION

The clear lower alcohol-free hydrocortisone solutions of this invention are comprised of up to 2% hydrocortisone, 15–30% polyethylene glycol 1300–1600 MWR, 15–30% propylene glycol, 5–20% glycerin, 3–12.4% sodium dioctyl sulfosuccinate, buffers, preservatives and water to make up to 100%. Micronized hydrocortisone is preferred as the smaller particle size provides for more rapid dissolution.

The amount of micronized hydrocortisone is preferably 1% w/v, the maximum concentration currently allowed in non-prescription hydrocortisone products. Citric acid and sodium citrate at 0.2% w/v each are used to buffer the solutions at about pH 4.9–5.4. Preservatives are selected from methylparaben, propylparaben, sodium benzoate, Glydant®, Phenoxetol®, Phenonip®, benzalkonium chloride and benzyl alcohol. The anionic surfactant sodium dioctyl sulfosuccinate, preferably the composition identified as Monowet MO-84 R2W® (MONA Industries, Patterson, N.J.) which contains 16% by weight of propylene glycol, is effective in facilitating solution of hydrocortisone in polyethylene glycol, propylene glycol and glycerin mixtures. The following examples are included to illustrate the various formulations useful in this invention and the processes for their preparation. These examples are included for illustrative purposes only and are not to be construed as limiting to this disclosure in any way. In the following examples certain ingredients are identified by trade names and are identified as follows:

Phenoxetol® is 2-phenylethanol.

Phenonip® is a mixture comprised of 2-phenoxyethanol (>70%), methyl p-hydroxybenzoate (>15%), ethyl p-hydroxybenzoate (<5%), propyl p-hydroxybenzoate (<5%), and butyl p-hydroxybenzoate (<10%).

Methylparaben is methyl p-hydroxybenzoate.

Propylparaben is propyl p-hydroxybenzoate.

Polyethylene glycol is a polyoxyethylene polymer of the formula HO—(CH$_2$CH$_2$O)$_n$—H commercially available in several molecular weight ranges from about 200 to over 8,000. The preferred polyethylene glycol is polyethylene glycol which has a molecular weight range (MWR) from about 1300 to about 1600.

EXAMPLE 1

| RAW MATERIAL | % W/V |
|---|---|
| Hydrocortisone Micronized | 1.00 |
| Polyethylene Glycol 1300–1600 MWR | 25.0 |
| Propylene Glycol | 25.8 |
| Glycerin 99% | 10.0 |
| Sodium Dioctyl Sulfosuccinate | 4.2 |
| Methylparaben | 0.150 |
| Phenoxetol | 1.00 |
| Citric Acid | 0.200 |
| Sodium Citrate | 0.200 |
| Water | q.s. to 100 ml |

Place the polyethylene glycol, propylene glycol, and sodium dioctyl sulfosuccinate in a suitable mixing container equipped with a mixer. Adjust the temperature to 60°–65° C.

Add and dissolve the micronized hydrocortisone in the polyethylene glycol/propylene glycol/sodium dioctyl sulfosuccinate mixture maintained at 60°–65° C.

Concurrently, place the glycerin in a suitable mixing container equipped with a mixer. Adjust the temperature to 85° C.

Add and dissolve the methylparaben in the glycerin. Continue mixing until a clear solution is obtained. Cool to 50° C.

Add the methylparaben solution to the hydrocortisone solution.

Dissolve the sodium citrate and citric acid in water in about a 1% concentration and add the solution to the hydrocortisone solution.

Add the Phenoxetol to the hydrocortisone solution.

Dilute the hydrocortisone solution to 100% volume with water. Continue mixing for ten minutes.

EXAMPLE 2

| RAW MATERIAL | % W/V |
|---|---|
| Hydrocortisone Micronized | 1.00 |
| Polyethylene Glycol 1300–1600 MWR | 25.0 |
| Propylene Glycol | 25.8 |
| Glycerin 99%, | 10.0 |
| Sodium Dioctyl Sulfosuccinate | 4.20 |
| Methylparaben | 0.150 |
| Phenonip | 0.50 |
| Citric Acid | 0.200 |
| Sodium Citrate | 0.200 |
| Water | q.s. to 100 ml |

Place the polyethylene glycol, propylene glycol and sodium dioctyl sulfosuccinate in a suitable mixing container equipped with a mixer. Adjust the temperature to 60°–65° C.

Add and dissolve the micronized hydrocortisone in the polyethylene glycol/propylene propylene glycol/sodium dioctyl sulfosuccinate mixture maintained at 60°–65° C.

Concurrently, place the glycerin in a suitable mixing container equipped with a mixer. Adjust the temperature to 85° C.

Add and dissolve the methylparaben in the glycerin. Continue mixing until a clear solution is obtained. Cool to 50° C.

Add the methylparaben solution to the hydrocortisone solution.

Dissolve the sodium citrate and citric acid in water at about a 1% concentration and add the solution to the hydrocortisone solution.

Add the Phenonip to the hydrocortisone solution.

Dilute the hydrocortisone solution to 100% volume with water. Continue mixing for ten minutes.

EXAMPLE 3

| RAW MATERIAL | % W/V |
|---|---|
| Hydrocortisone Micronized | 1.00 |
| Polyethylene Glycol 1300–1600 MWR | 25.0 |
| Propylene Glycol | 25.8 |
| Glycerin 99% | 10.0 |
| Sodium Dioctyl Sulfosuccinate | 4.20 |
| Methylparaben | 0.150 |
| Benzyl Alcohol | 1.00 |
| Citric Acid | 0.200 |
| Sodium Citrate | 0.200 |
| Water | q.s. to 100 ml |

Place the polyethylene glycol, propylene glycol and sodium dioctyl sulfosuccinate in a suitable mixing container equipped with a mixer. Adjust the temperature to 60°–65° C.

Add and dissolve the micronized hydrocortisone in the polyethylene glycol/propylene glycol/sodium dioctyl sulfosuccinate mixture maintained at 60°–65° C.

Concurrently, place the glycerin in a suitable mixing container equipped with a mixer. Adjust the temperature to 85° C.

Add and dissolve the methylparaben in the glycerin. Continue mixing until a clear solution is obtained.

Add the methylparaben solution to the hydrocortisone solution.

Dissolve the sodium citrate and citric acid in water at about a 1% concentration and add the solution to the hydrocortisone solution.

Add the benzyl alcohol to the hydrocortisone solution.

Dilute the hydrocortisone solution to 100% volume with water. Continue mixing for ten minutes.

EXAMPLE 4

| RAW MATERIAL | % W/V |
|---|---|
| Hydrocortisone Micronized | 1.00 |
| Polyethylene Glycol 1300–1600 MWR | 25.0 |
| Propylene Glycol | 25.8 |
| Glycerin 99% | 10.0 |
| Sodium Dioctyl Sulfosuccinate | 4.20 |
| Methylparaben | 0.150 |
| Propylparaben | 0.100 |
| Phenoxetol | 1.00 |
| Citric Acid | 0.200 |
| Sodium Citrate | 0.200 |
| Water | q.s. to 100 ml |

Place the polyethylene glycol, propylene glycol and sodium dioctyl sulfosuccinate in a suitable mixing container equipped with a mixer. Adjust the temperature to 60°–65° C.

Add and dissolve the micronized hydrocortisone in the polyethylene glycol/propylene glycol/sodium dioctyl sulfosuccinate mixture maintained at 60°–65° C.

Concurrently, place the glycerin in a suitable mixing container equipped with a mixer. Adjust the temperature to 85° C.

Add and dissolve the methylparaben and propylparaben in the glycerin. Continue mixing until a clear solution is obtained.

Add the methylparaben/propylparaben solution to the hydrocortisone solution.

Dissolve the sodium citrate and citric acid in water at about a 1% concentration and add the solution to the hydrocortisone solution.

Add the Phenoxetol to the hydrocortisone solution.

Dilute the hydrocortisone solution to 100% volume with water. Continue mixing for ten minutes.

EXAMPLE 5

| RAW MATERIAL | % W/V |
|---|---|
| Hydrocortisone Micronized | 1.00 |
| Polyethylene Glycol 1300–1600 MWR | 25.0 |
| Propylene Glycol | 25.8 |
| Glycerin 99% | 10.0 |
| Sodium Dioctyl Sulfosuccinate | 4.20 |
| Methylparaben | 0.200 |
| Propylparaben | 0.100 |
| Benzyl Alcohol | 1.00 |
| Citric Acid | 0.200 |
| Sodium Citrate | 0.200 |
| Water | q.s. to 100 ml |

Place the polyethylene glycol, propylene glycol and sodium dioctyl sulfosuccinate in a suitable mixing container equipped with a mixer. Adjust the temperature to 60°–65° C.

Add and dissolve the micronized hydrocortisone in the polyethylene glycol/propylene glycol/sodium dioctyl sulfosuccinate mixture maintained at 60°–65° C.

Concurrently, place the glycerin in a suitable mixing container equipped with a mixer. Adjust the temperature to 85° C.

Add and dissolve the methylparaben and propylparaben in the glycerin. Continue mixing until a clear solution is obtained. Cool to 50° C.

Add the methylparaben/propylparaben solution to the hydrocortisone solution.

Dissolve the sodium citrate and citric acid in water at about a 1% concentration and add the solution to the hydrocortisone solution.

Add the benzyl alcohol to the hydrocortisone solution.

Dilute the hydrocortisone solution to 100% volume with water. Continue mixing for ten minutes.

EXAMPLE 6

| RAW MATERIAL | % W/V |
|---|---|
| Hydrocortisone Micronized | 1.50 |
| Polyethylene Glycol 1300–1600 MWR | 25.0 |
| Propylene Glycol | 26.12 |
| Glycerin 99% | 10.00 |
| Sodium Dioctyl Sulfosuccinate | 5.88 |
| Methylparaben | 0.20 |
| Sodium Citrate | 0.20 |
| Citric Acid | 0.20 |
| Water | q.s. to 100 ml |

The 1.5% hydrocortisone formulation is prepared by following the same sequences of procedures as given in Examples 1–5.

EXAMPLe 7

| RAW MATERIAL | % W/V |
|---|---|
| Hydrocortisone Micronized | 2.00 |
| Polyethylene Glycol 1300–1600 MWR | 25.0 |
| Propylene Glycol | 27.40 |
| Glycerin 99% | 10.00 |
| Sodium Dioctyl Sulfosuccinate | 12.4 |
| Methylparaben | 0.20 |
| Sodium Citrate | 0.20 |
| Citric Acid | 0.20 |
| Water | q.s. to 100 ml |

The 2.0% hydrocortisone formulation is prepared by following the same sequences of procedures as given in Examples 1–5.

Those skilled in the art of formulation will realize that still other formulations containing hydrocortisone and sodium dioctyl sulfosuccinate may provide clear solutions of hydrocortisone. Other preservatives including, but not limited to sodium benzoate, benzalkonium chloride and DMDM hydantoin [1,3-bis(hydroxymethyl)-5,5-dimethyl-2,4-diazolidinedione] may also be used effectively.

The solutions prepared in the preceding examples remain clear on standing at room temperature.

What is claimed is:

1. A clear, aqueous, alcohol-free composition comprising about 1% to about 2% hydrocortisone, about 15–30% polyethylene glycol 1300–1600 MWR, about 15–30% propylene glycol, about 5–20% glycerin, about 3–15% sodium dioctyl sulfosuccinate, buffers, preservatives, and water to make up to final volume.

2. A composition according to claim 1 wherein the hydrocortisone content is about one percent of the total weight.

3. A composition according to claim 1 wherein the hydrocortisone content is about 1.5 percent of the total weight.

4. A composition according to claim 1 wherein the hydrocortisone content is about 2.0 percent of the total weight.

5. The composition according to claim 1 wherein the composition is comprised of about 1% hydrocortisone micronized, about 20–25% polyethylene glycol 1300–1600 MWR, about 20–30% propylene glycol, about 10% glycerin, about 5% sodium dioctyl sulfosuccinate, buffers, preservatives and water to make up to final volume.

6. A process for preparing a clear, aqueous alcohol-free composition comprising dissolving hydrocortisone in a mixture of polyethylene glycol 1300–1600 MWR, propylene glycol and sodium dioctyl sulfosuccinate at a temperature of about 60°–65° C., adding thereto glycerin or a mixture prepared at about 80°–85° C. containing one or more preservatives dissolved in glycerin and subsequently cooled to about 50° C., adding to the combined solutions the buffers citric acid and sodium citrate as about 1% aqueous solutions in water and then adding to the combined solutions phenoxytol or benzyl alcohol if used, thickeners, fragrances and topical dermatological agents, followed by adding sufficient water to make up to final volume.

7. A wipe for treatment of dermatological conditions comprised of a tissue impregnated with a composition according to claim 1.

8. A wipe according to claim 7 which is selected from a rayon web bonded with an acrylic copolymer binder or a tissue comprised of 60% wool pulp, 30% rayon, and 10% polyester/polyethylene.

9. The composition of claim 1 further comprising at least one preservative selected from the group consisting of methyl paraben, propyl paraben, phenoxyethanol or benzyl alcohol.

10. The process of claim 6 wherein the hydrocortisone is micronized hydrocortisone.

11. The process of claim 6 wherein the glycerin further comprises at least one preservative selected from the group consisting of methyl paraben, propylparaben, phenoxyethanol or Phenonip.

\* \* \* \* \*